United States Patent
Lacey

(10) Patent No.: US 11,958,126 B2
(45) Date of Patent: Apr. 16, 2024

(54) CONTAINERS FOR RETAINING ANESTHETIC AGENT AND MANUFACTURING METHODS THEREOF

(71) Applicant: GE Precision Healthcare LLC, Wauwatosa, WI (US)

(72) Inventor: Joseph J. Lacey, Madison, WI (US)

(73) Assignee: GE Precision Healthcare LLC, Wauwatosa, WI (US)

( * ) Notice: Subject to any disclaimer, the term of this patent is extended or adjusted under 35 U.S.C. 154(b) by 662 days.

(21) Appl. No.: 17/063,817

(22) Filed: Oct. 6, 2020

(65) Prior Publication Data

US 2022/0105588 A1    Apr. 7, 2022

(51) Int. Cl.
| | |
|---|---|
| B23K 20/00 | (2006.01) |
| A61J 1/05 | (2006.01) |
| A61J 1/14 | (2023.01) |
| B23K 1/00 | (2006.01) |
| B23K 20/12 | (2006.01) |
| C23C 30/00 | (2006.01) |
| F17C 3/00 | (2006.01) |
| B23K 101/12 | (2006.01) |

(52) U.S. Cl.
CPC ............ B23K 20/122 (2013.01); A61J 1/05 (2013.01); A61J 1/1468 (2015.05); A61J 1/1475 (2013.01); B23K 1/0008 (2013.01); C23C 30/00 (2013.01); F17C 3/00 (2013.01); *B23K 2101/12* (2018.08); *F17C 2203/0646* (2013.01); *F17C 2209/2109* (2013.01); *F17C 2209/221* (2013.01); *F17C 2270/02* (2013.01)

(58) Field of Classification Search
CPC .. B23K 20/125; B23K 20/1265; B23K 28/02; B23K 20/1245; B23K 11/11; B23K 20/123; B23K 20/1255; B23K 20/122; B23K 20/126; B23K 2103/18; B23K 1/0008; B23K 11/16; B23K 20/1225; B23K 2101/12
See application file for complete search history.

(56) References Cited

U.S. PATENT DOCUMENTS

| | | |
|---|---|---|
| 5,460,317 A | 10/1995 | Thomas et al. |
| 6,230,957 B1 | 5/2001 | Arbegast et al. |
| 2004/0118899 A1* | 6/2004 | Aota ................. B23K 20/1255 228/2.1 |
| 2006/0032891 A1 | 2/2006 | Flak et al. |
| 2006/0054252 A1 | 3/2006 | Sankaran et al. |

(Continued)

OTHER PUBLICATIONS

Mishra, et al. "Friction stir welding and processing," Materials Science and Engineering R 50, Aug. 18, 2005, 1-78, Elsevier B.V.

*Primary Examiner* — Erin B Saad

(57) ABSTRACT

A method for making a container for retaining anesthetic agent. The method includes creating two or more parts each having a mating surface, where the container is formed when the mating surfaces of the two or more parts are coupled together, and where a first part of the two or more parts is formed of a material having pores defined within the mating surface thereof. The method further includes processing the mating surface of the first part via friction stir welding to reduce the pores defined therein. The method further includes coupling the two or more parts together such that the mating surfaces contact to create the container configured to retain the anesthetic agent therein.

14 Claims, 8 Drawing Sheets

(56) References Cited

U.S. PATENT DOCUMENTS

| | | | |
|---|---|---|---|
| 2014/0261900 A1* | 9/2014 | Maurer | C22F 3/00 |
| | | | 148/512 |
| 2015/0375335 A1* | 12/2015 | Liu | B23K 20/126 |
| | | | 219/78.13 |
| 2016/0318120 A1* | 11/2016 | Okada | B23K 20/126 |
| 2019/0143442 A1* | 5/2019 | Ohashi | B23K 20/12 |
| | | | 428/172 |
| 2022/0105588 A1* | 4/2022 | Lacey | B23K 1/0008 |
| 2023/0013259 A1* | 1/2023 | Miyawaki | B23K 28/02 |
| 2023/0014926 A1* | 1/2023 | Miyawaki | B23K 11/115 |
| 2023/0019177 A1* | 1/2023 | Miyawaki | B23K 20/125 |

* cited by examiner

CONTAINERS FOR RETAINING ANESTHETIC AGENT AND MANUFACTURING METHODS THEREOF

FIELD

The present disclosure generally relates to containers for retaining anesthetic agent and manufacturing methods thereof, and more particularly to joining cast metal via brazing by healing porosity in the castings so as to enable oven brazing, which is very advantageous in anesthesia applications for creating gas manifolds and liquid anesthesia containers.

BACKGROUND

Anesthesia machines are devices particularly configured for administering anesthetic agent to a patient with high precision and accuracy. The anesthetic agent is at some point typically held within a reservoir within the anesthesia machine, for example in a sump or pathway defined within a material often made of metal. A variety of anesthetic agents may be administered, each having its own storage and chemical reactivity limitations that must be safely handled by the anesthesia machine. As will be discussed below, these reservoirs are typically formed by the union of two or more parts, typically by joining with bolts and employing gasket seals. In order to deliver anesthetic gas to the patient the machine contains gas manifolds to enable gas blending and transport.

Exemplary anesthesia machines to which the presently disclosed methods may be applied include the Aisys $CS^2$, Adance $CS^2$, and Carestation 600 Series Anesthesia Delivery Systems, as well as Aladin2 cassettes, produced by GE Healthcare.

SUMMARY

This Summary is provided to introduce a selection of concepts that are further described below in the Detailed Description. This Summary is not intended to identify key or essential features of the claimed subject matter, nor is it intended to be used as an aid in limiting the scope of the claimed subject matter.

One embodiment of the present disclosure generally relates to a method for making a container for retaining anesthetic agent. The method includes creating two or more parts each having a mating surface, where the container is formed when the mating surfaces of the two or more parts are coupled together, and where a first part of the two or more parts is formed of a material having pores defined within the mating surface thereof. The method further includes processing the mating surface of the first part via friction stir welding to reduce the pores defined therein. The method further includes coupling the two or more parts together such that the mating surfaces contact to create the container configured to retain the anesthetic agent therein.

Another embodiment generally relates to a metallic container for retaining a gas or liquid. A first part made of a cast material has a first non-mating surface with pores, and has a first mating surface processed via friction stir welding to be substantially free of pores. A second part is made of a metallic material having a second mating surface and a second non-mating surface. The first part and the second part are coupled together such that the first mating surface contacts the second mating surface such that a reservoir is formed by the first part and the second part when coupled together. The reservoir is configured to retain the gas or liquid.

Another embodiment generally relates to a method for making a container for retaining a gas or liquid. The method includes casting a first part of a metallic material, where the first part has a first mating surface and a non-mating surface, and where the metallic material has pores defined within the first mating surface. The method further includes processing the first mating surface of the first part via friction stir welding to reduce the pores defined therein and obtaining a second part made of a metallic material. The second part has a second mating surface and a second non-mating surface, where at least one of the first part and the second part defines a passageway. The method further includes brazing the first part and the second part together such that the first mating surface of the first part is in contact with the second mating surface of the second part such that a reservoir is formed between the first non-mating surface of the first part and the second non-mating surface of the second part when the first part and the second part are brazed together, where the reservoir is configured to retain the gas or liquid therein, and where the container is configured such that the gas or liquid exits the reservoir only via the passageway.

Various other features, objects and advantages of the disclosure will be made apparent from the following description taken together with the drawings.

BRIEF DESCRIPTION OF THE DRAWINGS

The present disclosure is described with reference to the following Figures.

DETAILED DISCLOSURE

Figure 1:
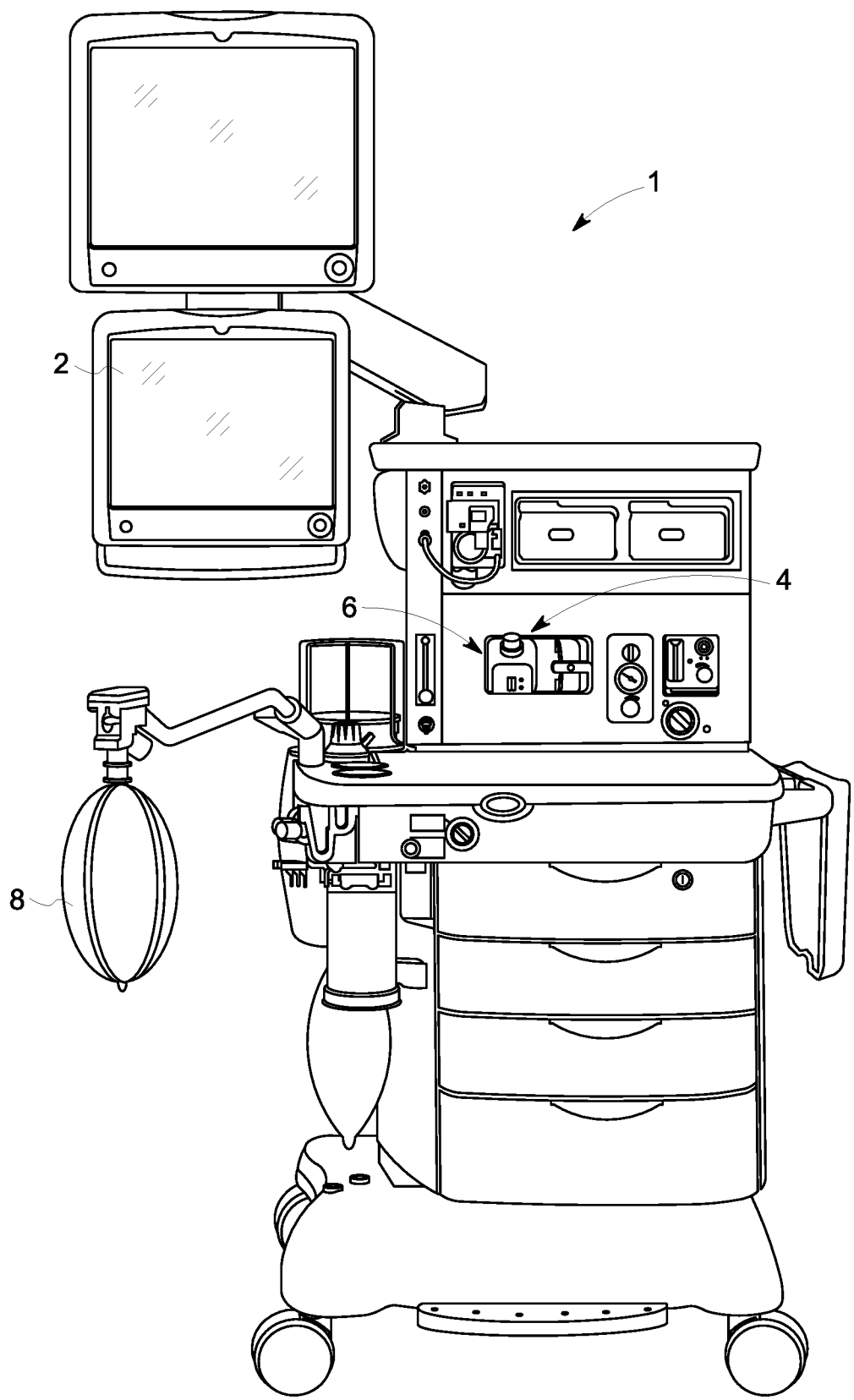
FIG. 1 depicts an exemplary anesthesia machine including anesthetic agent containers made according to the present disclosure.

The present disclosure generally relates to containers for retaining anesthetic agent or creating manifolds for gases or fluids used with medical devices, and improved methods for making such containers. FIG. 1 depicts a medical device 1, which in the present example is an anesthesia machine including one or more containers 6 for retaining gases or fluids according to the present disclosure. The medical device 1 presently shown includes a display 2 for operating the medical device 1 in conjunction with a manual ventilation bag 8, as is customary within the field of anesthesia machines. FIG. 1 further shows an anesthetic agent cassette 4, which includes a sump as the container 6 for retaining anesthetic agent, such as desflurane or isoflurane, for example. The anesthesia machine delivers the anesthetic agent from the container 6 to the patient in a controlled manner according to processes presently known in the art.

The present inventor has recognized that the particular methods used for manufacturing the manifolds and containers that retain gases or fluids, such as those used within medical devices, are often costly and/or highly restrictive with respect to the shapes in which the reservoirs may be formed. For example, the inventor has recognized that manufacturing parts via casting, such as through sand casting or permanent mold casting methods known in the art, provide for great flexibility in the shapes and dimensions of the resultant part. However, it is recognized that cast parts suffer from significant surface porosity, a condition that is not present in other, more costly methods of fabrication.

A common practice for forming manifolds and containers that need to be gas tight is to machine from billet stock. In one common method, passages ways are formed by drilling into the block. To make continuous flow paths, drilled holes are intersected, which leaves one side of the drilled hole that needs to be plugged (cross drilled manifold). Cross drilled manifolds are prone to leakage and leaving metal chips inside the part (potential for O2 fire source, blockage of valves, and/or other problems known in the art). While cheap to make, these manifolds are limited in the ability to create complex passageways.

Another common approach is to split the manifold into two or more sections (two sections is typical), and to machine in the passageways into one block and use a cover block to seal. The cover block can be oven brazed if blocks are created from billet stock, meaning a solid block that is heavily machined to create passages. However, this is more expensive and involved than net shaping the passages ways.

Another technique is to put a compliant sealing gasket between the blocks and use multiple screws to make a leak tight manifold. However, this leads to excessive number of bolts and renders designs at risk for leaking.

Likewise, the present inventor has recognized that oven brazing is a convenient and cost-effective method used in many industries for joining metal parts, which may be especially useful for making parts that have complicated internal flow passages (e.g. cold plates). However, oven brazing is not an effective or reliable means for joining parts that are cast, as the surface porosity discussed above leads to unpredictable braze joints, poor quality of joints, and a consequent high risk of leaking the liquids or gases contained therein. Consequently, cast parts cannot be used for creating these reservoirs and passageways, thus requiring higher cost alternatives for manufacturing parts that enable brazed, including substantial additional machining. This may be particularly extreme in the cases of sumps having a substantial size and/or depth (for example, see FIG. 3), which require extensive machining to remove sufficient material to form a reservoir.

Accordingly, the present inventor has recognized that if cost-effective cast parts could somehow be healed, meaning the surface porosity reduced or eliminated such that oven brazing once again becomes feasible, these cast parts could be joined in a reliable manner using the same oven brazing techniques already known. Through experimentation and development, the present inventor has identified that by processing the surfaces of parts intended to be oven brazed together using a friction stir welding device, the areas processed are locally healed and substantially free of pores, thus enabling brazing. In this alternative use of friction stir welding (FSW), the FSW is not used for welding as it typically would be, but instead the FSW is simply run within the area where the braze joint is to be performed, whereby this visco-plastic stirring of the metal eliminates the porosity and thus enables brazing. Additional information regarding friction stir welding and processing methods presently known in the art is provided in U.S. Pat. No. 5,460,317, as well as the *Materials Science and Engineering Reports* journal publication of *Friction stir welding and processing* (Mishra & Ma, August 2005), which are each incorporated by reference herein.

It will be recognized the healing is described as being "substantially" free of pores because the surfaces need to be essentially free of porosity to provide for reliable brazing between parts. When using wrought stock (billet metal blocks), there is no porosity to contend with. However, all cast parts have porosity to differing degrees. The reason this is problematic is that during the heating process to braze, the trapped gas in the porosity expands and can escape or rupture the cavity. This blows the molten braze material out of the joint. Additionally, open porosity leads to braze material flowing away from joint and filling openings removing braze material from intended area. Thus, porosity needs to be eliminated at the braze joint, which is what the FSW process does. For the purposes of this disclosure, being free of porosity will mean effectively free of porosity, meaning that after healing the surface with the FSW tool, the surface condition is essentially the same as would be present for wrought plates or blocks of metal, and thus is now suitable for an oven brazing process, for example.

Figure 7:
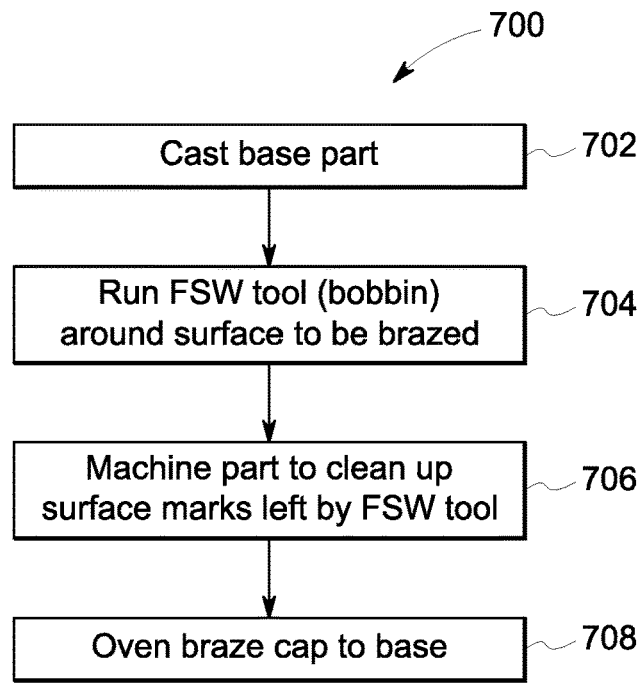
FIG. 7 depicts an exemplary method for producing parts according to the present disclosure.

An exemplary method 700 according to the present disclosure is shown in FIG. 7. The process 700 consists of casting at least a base part in step 702, such as via sand casting, in a manner known in the art. A cap part may also be formed via casting, or may instead be fabricated through methods not resulting in surface porosity (or being substantially or sufficiently free of pores to enable brazing). The method 700 proceeds with step 704, whereby an FSW tool or bobbin is used to provide visco-plastic stirring of the cast part in the regions in which brazing will eventually be performed. The result is a surface in which the porosity has been reduced or eliminated, effectively healing the surface for future brazing or other coupling methods. As stated above, "healing" means that the processed regions or surfaces of the part are substantially or sufficiently free of pores so as to enable efficient and effecting brazing. Step 706 then provides for machining or otherwise processing the surface to clean up any surface marks or other surface conditions left by the FSW tooling process. It will be recognized that in certain embodiments, the FSW tooling process may not create surface marks or conditions requiring processing or cleaning up before proceeding. Finally, a second part, in the present example, the cap, may be oven brazed to the base in step 708, using standard practices for brazing as known in the art.

Figure 8:
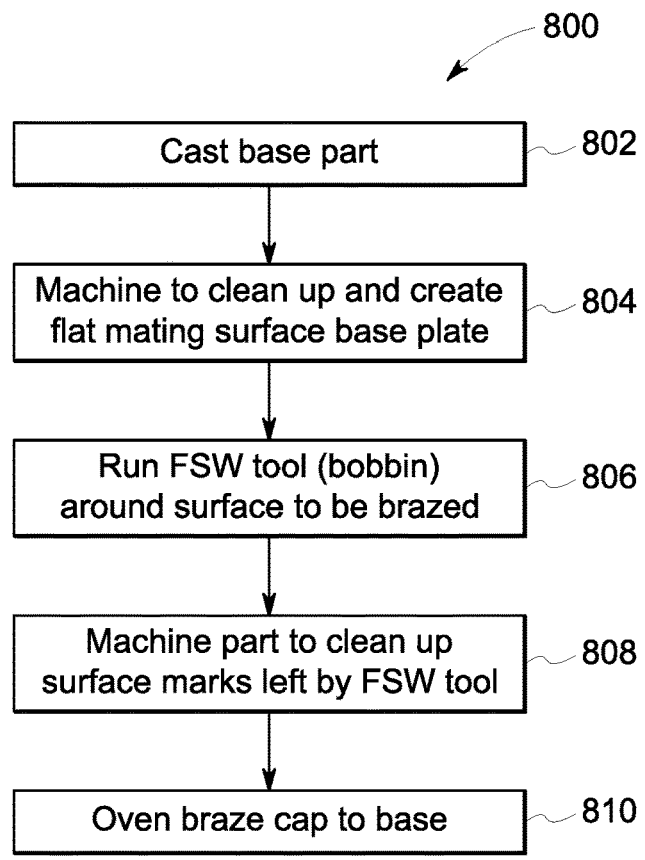
FIG. 8 depicts another exemplary method for producing parts according to the present disclosure.

The inventor recognized that in certain examples, it is further necessary to machine or otherwise clean up the surface of a cast part before the processing with the FSW tool may be effectively completed. This alternative process 800 is shown in FIG. 8, whereby step 804 performs this clean up the cast part from step 802 to create a flat mating surface to be healed and later brazed with the second part or cap. It should be noted that oven brazing by its nature requires very flat parallel surfaces at a bonding joint. Therefore, even billet parts typically require a secondary machining pass or process along the surfaces to be joined.

Figure 2:
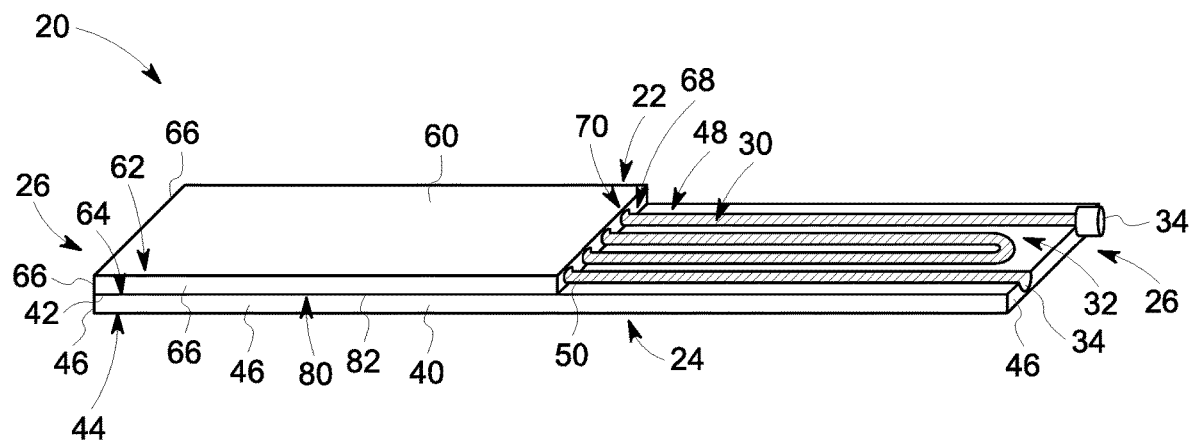
FIG. 2 is an isometric view of an exemplary container made according to the present disclosure.

FIG. 2 shows an exemplary container 20 produced using a method according to the present disclosure, specifically with a portion of the second part 60 cut away to shown an interior thereof. The container 20 may serve as a more cost effectively built cold plate, or other reservoir 30 in which a serpentine, complicated, or otherwise labor-intensive path may be cost effectively produced via simpler methods, such as casting. The container 20 extends between a top 22 and bottom 24, having sides 26 therebetween. The container 20 of the present embodiment is specifically formed of a first part 40 coupled to a second part 60 at a seam 80, which in the present example is a weld of brazing material 82 as discussed above. The first part 40 extends between a top 42 and bottom 44 with sides 46 therebetween, and likewise the second part 60 extends between a top 62 and bottom 64 with sides 66 therebetween. The first part 40 has a mating surface 48 intended to be in contact with, or facing, and welded to the mating surface 68 of the second part 60. Additionally, a non-mating surface 50 is defined within the first part 40, which forms the basis for defining at least part of the reservoir 30 for containing a gas or fluid, such as an anesthetic agent or coolant, for example. As discussed above, the reservoir 30 may have curves 32 or other features that are most cost effectively formed via methods such as cast molding.

In the example shown, the second part 60 also defines a non-mating surface 70 therein. However, it is not necessary that the reservoir 30 be defined within both the first part 40 and second part 60, and thus the non-mating surface 70 may not be a defined recess. In other words, a more cost-effective solution may be that the second part 60 is merely a cap in which the non-mating surface 70 is not recessed or defined therein. It will also be recognized that the first part 40 and second part 60 may be functionally reversed such that the first part 40 is a cap. Likewise, the container 20 may have more than two parts, such sample two caps that sandwich a central portion having the reservoir defined therein.

Ports 34 are also defined, in the present case within the one or more sides 26 of the container 20, providing fluid connectivity to the reservoir 30 from outside the container 20. In the present example, one port 34 is shown as merely the entrance to the reservoir 30 from outside the container 20, with another port 34 shown as a coupler or connector for interfacing with another conduit, for example. In the present example, the fluid or gas may flow in one port 34, through the reservoir 30, and out the other port 34. In other cases, such as shown in FIG. 3, only one port 34 is used to both fill and empty the reservoir 30 (although vents or other pressure normalizing devices may also be included to enable this process as known in the art, for example).

Since FIG. 1 shows a completed container 20, it will be recognized that the mating surfaces 48, 68 are substantially free of pores after having been healed according to the present disclosure, whereas the non-mating surfaces 50, 70 may still have pores (not having been treated with the FSW process). As discussed later below, other treatments may also be provided for the mating surfaces 48, 68 and/or non-mating surfaces 50, 70, such as platings or coatings.

Figure 3:
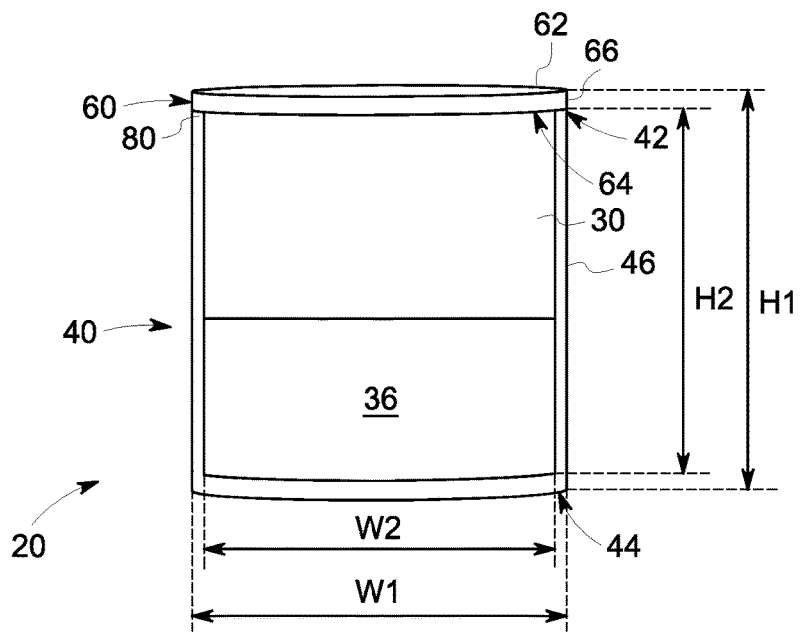
FIG. 3 is a front view of another exemplary container made according to the present disclosure.

FIG. 3 depicts another exemplary container 20 according to the present disclosure, in the present example resembling a sump such as incorporated in the medical device 1 of FIG. 1. In this embodiment, the container 20 has a height H1 and width W1, with the reservoir 30 defined therein to have a height H2 and width W2. As discussed above, the volume of the reservoir 30 in this case is substantial relative to that of the container 20. As such, this configuration would necessitate substantial machining if the first part 40 were produced other than by casting, such as extensive material removal. In this manner, the present disclosure provides a cost-effective method for creating a substantially sized reservoir 30 for containing anesthetic agent 36, for example, while still enabling oven brazing processes for coupling the first part 40 to the second part 60 at the seam 80.

In certain embodiments, a container such as the container 40 of FIG. 3 may form a gas manifold from a cast part and a machined billet part. Making gas manifolds from parts oven brazed together is one common method of creating leak tight manifolds. However, today such joining is restricted to using billet metal machining to shape, then oven brazing. By following the methods described in the present disclosure, net shaped cast parts can be used, saving cost and adding manufacturing flexibility for passage way design and still using the oven braze process which is proven cost effective manufacturing technique.

Figure 4:
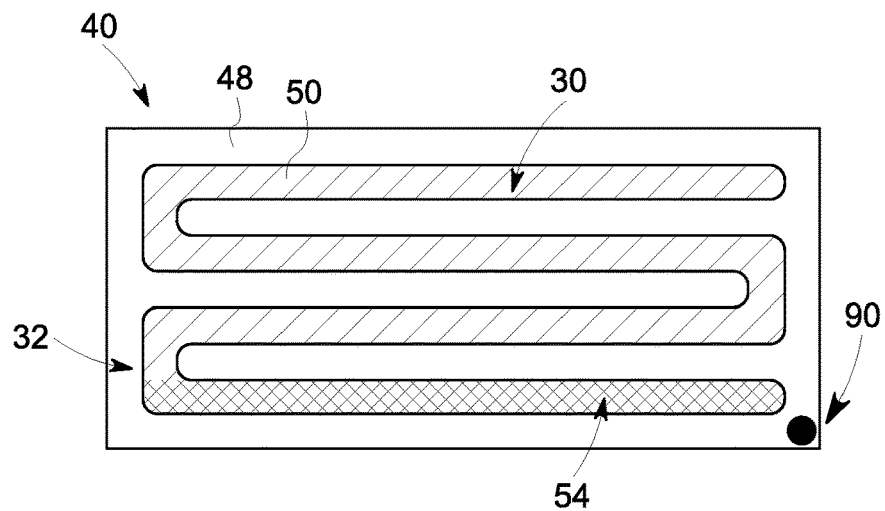
FIG. 4 is a sectional top view of the container shown in FIG. 2 prior to assembly.
Figure 5:
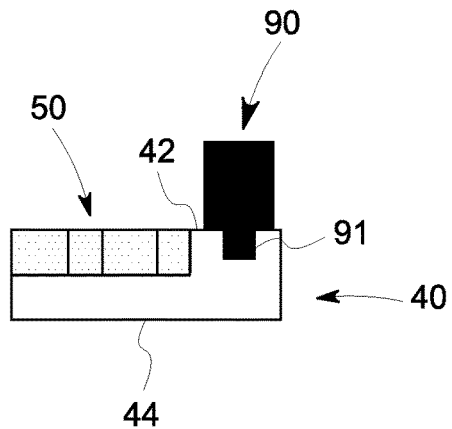
FIG. 5 is a sectional side view of the partial container of FIG. 4 shown being processed according to the present disclosure.

FIG. 4 depicts the first part 40 of FIG. 2 prior to brazing or otherwise coupling with the second part 60. In the embodiment shown, the reservoir 30 is at least partially formed by the non-mating surface 50 defined within the first part 40. As previously described, a mating surface 48 forms the other portion of the surface for the top 42 of the first part 40, which is the surface to be in contact with the second part 60. In the example shown, a portion of the non-mating surface 50 is shown treated with a treatment 54, such as nickel plating, which may be specifically chosen in a manner known in the art to prevent corrosion or other chemical interaction between the material of the first part 40 and the anesthetic agent or other gas or fluid being retained within the reservoir 30. FIG. 4 further depicts a starting point for a friction stir welder 90, which is shown in use in FIG. 5. As discussed above, the friction stir welder 90 is traced around the mating surface 48 of the first part 40 (and mating surface 68 of the second part 60 if also made of a porous material) with its bobbin 91 extending therein to cause the viscoplastic stirring. This visco-plastic stirring therefore eliminates or heals the surface porosity along the path in which the friction stir welder 90 travels.

Figure 6:
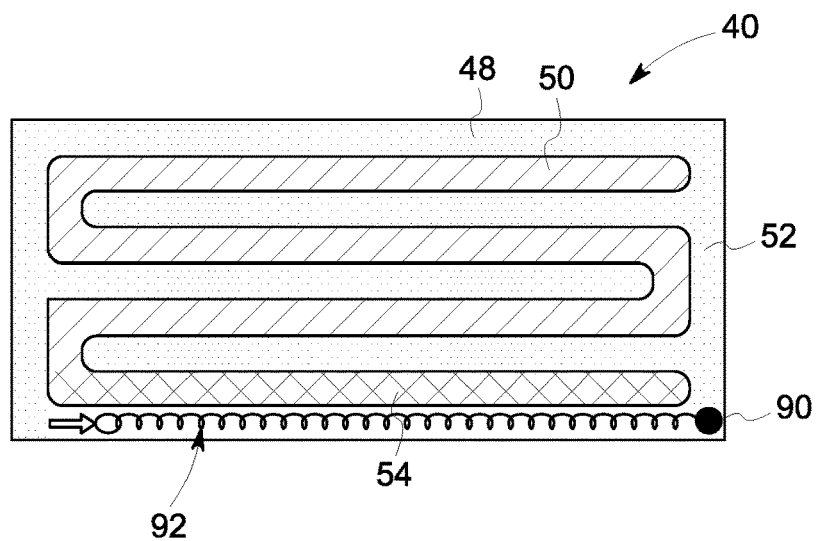
FIG. 6 is a top sectional view depicting the part of FIG. 4 mid-process according to the present disclosure.

FIG. 6 shows the pores 52 within the mating surface 48 of the first part 40, along with the partial treatment (shown as the spiraled line) via the friction stir welder 90 in healing and illuminating these pores 52. It will further be recognized that FIG. 6 also depicts residual surface conditions 92 left by the friction stir welder 90, which as previously discussed may require or benefit from subsequent machining to ensure a flat and smooth surface before oven brazing or other welding of the mating surface 48 takes place. Once the friction stir welder 90 has traced over the intended regions of the mating surface 48 of the first part 40, along with the mating surface 68 of the second part 60 as necessary, and any such surface conditions 92 are rectified (with this, porosity cured, finalized path shown as 93), the first part 40 and second part 60 are able to be welded together, such as by oven brazing, to form the container 20 shown in FIG. 2. It will be recognized that for the sake of clarity, the final path 93 is not shown in all figures, such as FIG. 2.

The present inventor has further recognized that the presently disclosed methods are not limited to healing for traditionally casted metals. For example, a new casting procedure known as ablation casting now enables sand casting of traditionally wrought only aluminum alloys, such as 6061. By using the presently disclosed methods in combination with ablation casting of traditional wrought alloys, complex assemblies from castings, forgings and machined components of the same alloy can be readily completed.

It will also be recognized that in addition to extending the types of assemblies that can be constructed using oven brazing, the presently disclosed methods also enable mixing of manufacturing processes such as casting, forging, and machined billet parts into single oven brazing assembly. While the foregoing has principally referred to applications within the medical devices industry, the present disclosure may also be applicable for making reservoirs and/or fluid pathways in other, such as cold plates for controllers in avionics, beverage dispensers, and/or the like.

Figure 9A:
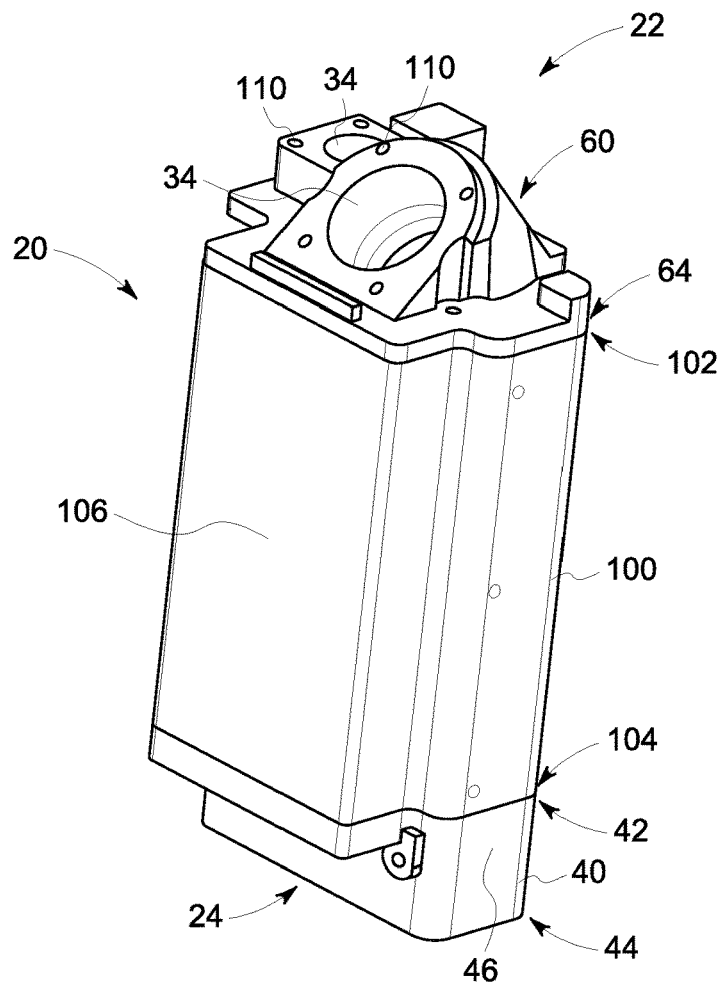
FIG. 9A is an isometric view of another exemplary container made according to the present disclosure.
Figure 9B:
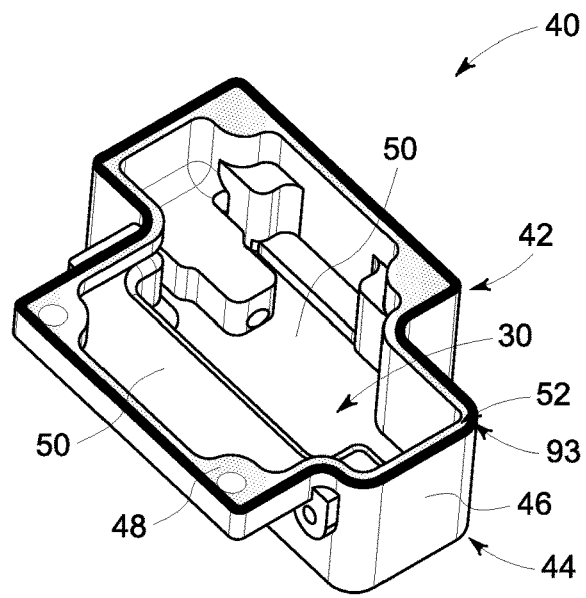
FIG. 9B depicts the first part of the container shown in FIG. 9A.
Figure 9C:
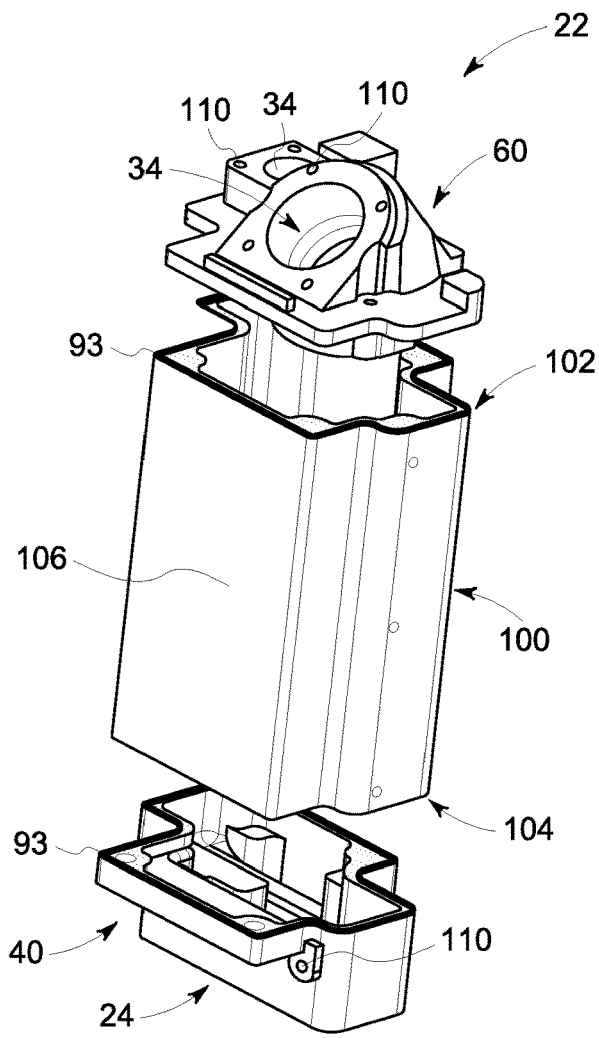
FIG. 9C is an exploded view of the container of FIG. 9A.
Figure 10A:
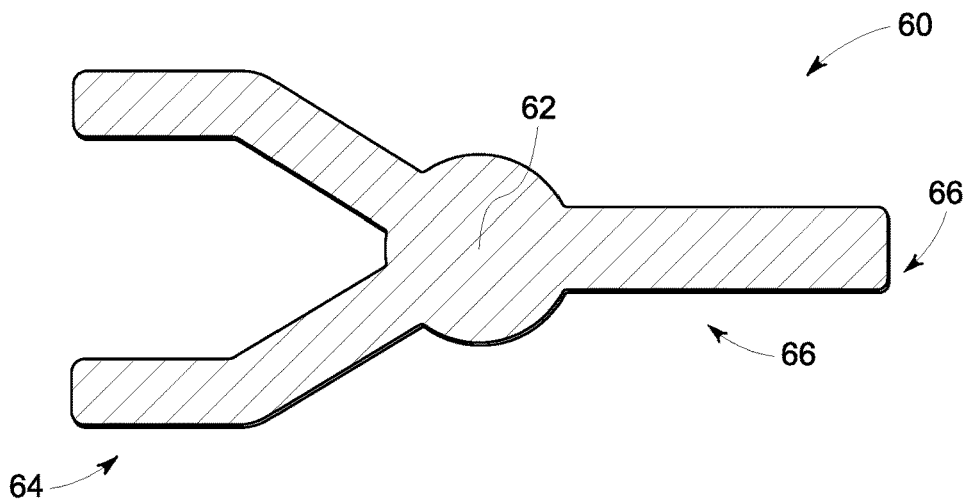
FIG. 10A is an isometric view of a first part for another exemplary container made according to the present disclosure.
Figure 10B:
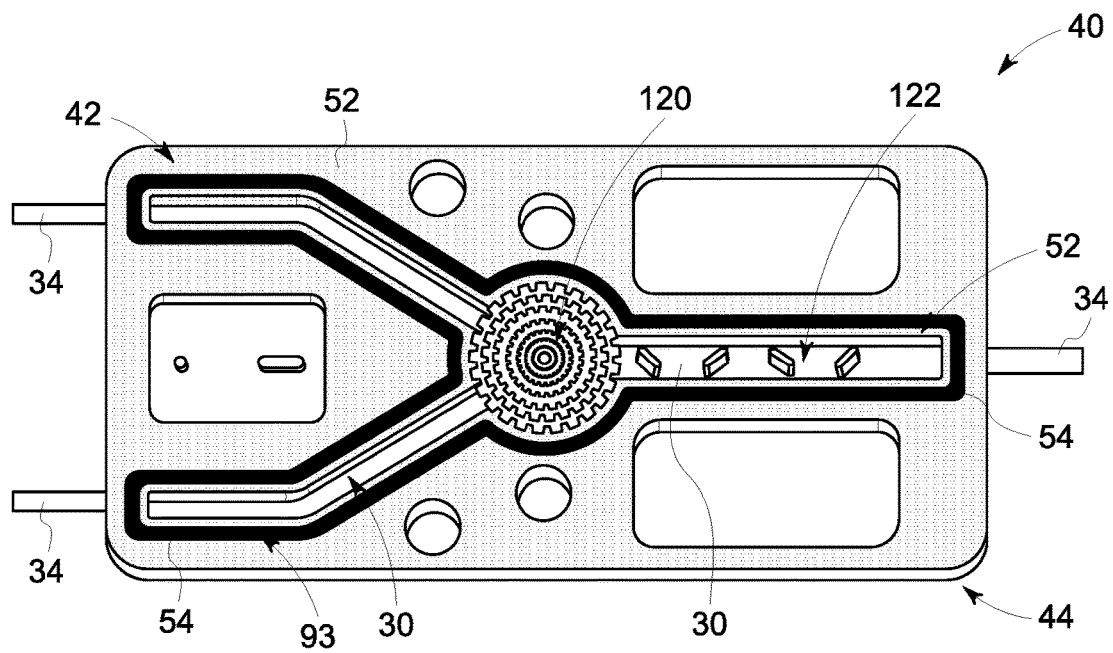
FIG. 10B is an isometric view of a second part corresponding to the first part of FIG. 10A.
Figure 10C:
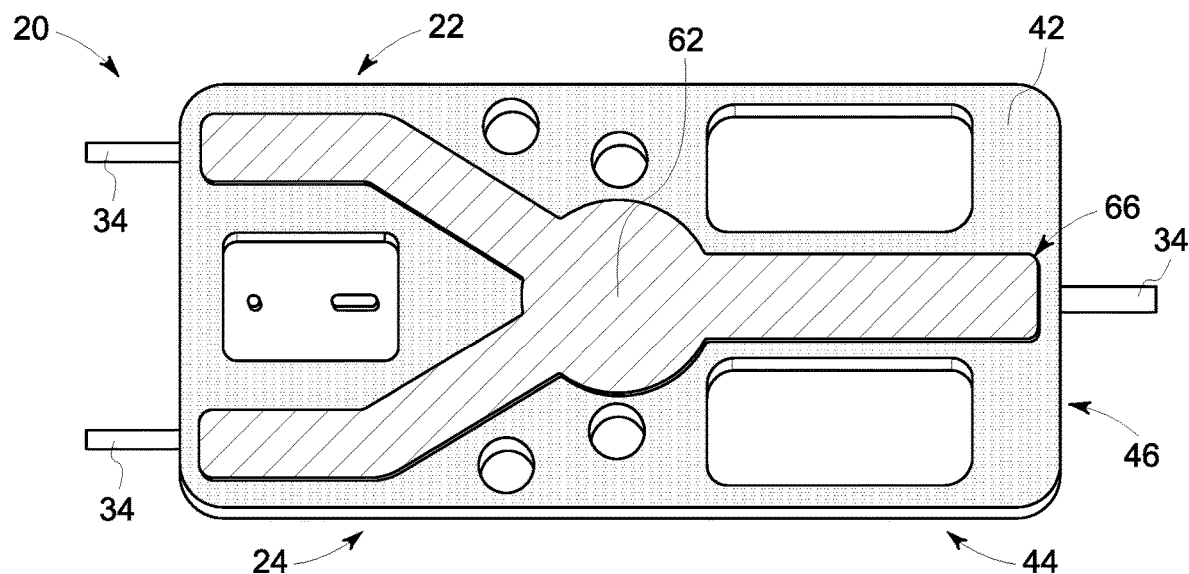
FIG. 10C is an isometric view of the container formed by the first and second parts of FIGS. 10A and 10B.

Additional exemplary containers 20 are provided in FIGS. 9A-9C and 10A-10C. In these examples, the container 20 of FIGS. 9A-9C is configured to be used as a sump within GE Healthcare's Serenity™ anesthesia machines for containing anesthetic agent therein, and the container 20 of FIGS. 10A-10C is a mixer for ensuring proper mixing of two incoming compounds merging from the ports 34 on the left side to the right side.

In the example of FIGS. 9A-9C, the container 20 includes a third part 100 that is sandwiched between first and second parts 40, 60 using the processes described above (e.g., using FSW to provide treatment 54 on the surfaces 48, 68, and 108 of the first, second, and third parts 40, 60, 100, respectively, to substantially eliminate porosity and permit brazing). It will be recognized that in certain examples, one of more of the first, second, and third parts 40, 60, 100 are produced by a method not having porosity, and thus not requiring treatment via FSW before brazing to other surfaces of other parts having received such treatments.

It will further be recognized that the part 20 of FIGS. 9A-9C, as with the others disclosed here, may still have the same fixation features 100 for coupling within the broader system, such as a medical device 1. Exemplary fixation features 100 include threaded openings for receiving screws or bolts, or other fastening techniques as known in the art.

FIGS. 10A-10C depict an exemplary mixer, such as may also be incorporated within GE Healthcare's Serenity™ anesthesia machines, other medical devices or non-medical devices requiring mixing of a gas or liquid with other gases or liquids, for example. In the example shown, the second part 60 is essentially a cover that is coupled to the first part 40 using the techniques described herein. In this example, it can be seen that much of the top 42 of the first part 40 does not require a treatment 54, but for the portion corresponding to the second part 60 (with may or may not itself require processing via FSW on its bottom 64 to enable coupling via brazing, for example). By allowing the first part 40 to be processed to cure or eliminate the porosity within the regions where the second part 60 will be coupled thereto, the first part 40 may be made via basic casting techniques that enable complicated paths and structures for a low relative cost. In the example of the mixer shown, mixing features 120, 122 are provided within the reservoir 30 defined within the first part 40, again via the casting thereof. By positioning these mixing features 120, 122 within the path between the ports 34 on the left of the container 20 and the exit via the port 34 on the right, proper mixing is ensured for the two incoming materials.

Figure 11:
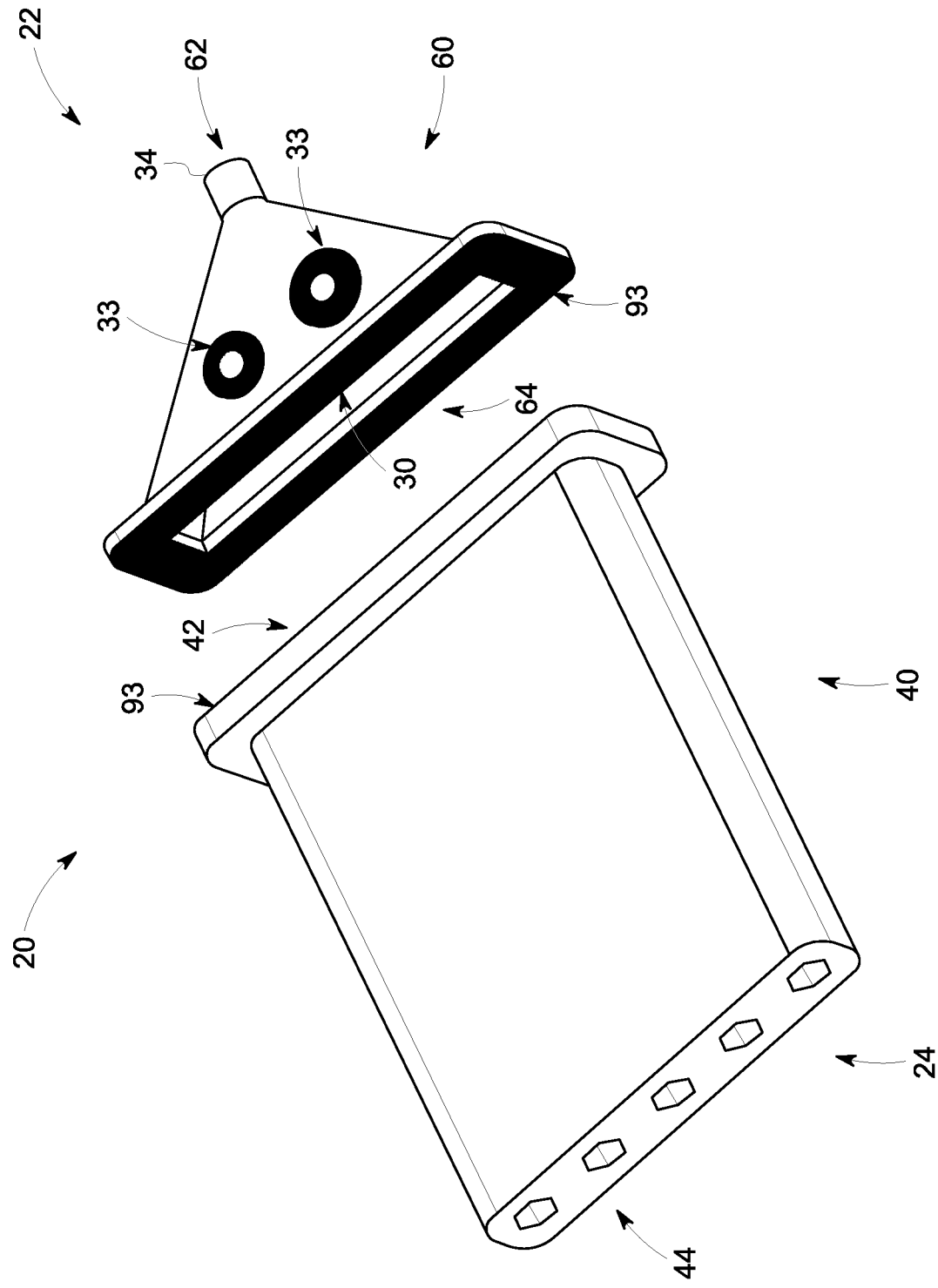
FIG. 11 is a isometric view of another exemplary container made according to the present disclosure.

It will be recognized that the presently disclosed methods may also be used to enable brazing of other components, including standoffs, tabs, or headers to a casting. Similarly, FIG. 11 shows a container 20 that, in addition to curing the porosity along the final paths 93 to couple the first part 40 to the second part 60 via brazing, the surfaces of port fittings 33 are also processed using the FSW tool as discussed above to enable brazing of fittings 34 here as well.

The functional block diagrams, operational sequences, and flow diagrams provided in the Figures are representative of exemplary architectures, environments, and methodologies for performing novel aspects of the disclosure. While, for purposes of simplicity of explanation, the methodologies included herein may be in the form of a functional diagram, operational sequence, or flow diagram, and may be described as a series of acts, it is to be understood and appreciated that the methodologies are not limited by the order of acts, as some acts may, in accordance therewith, occur in a different order and/or concurrently with other acts from that shown and described herein. For example, those skilled in the art will understand and appreciate that a methodology can alternatively be represented as a series of interrelated states or events, such as in a state diagram. Moreover, not all acts illustrated in a methodology may be required for a novel implementation.

This written description uses examples to disclose the invention, including the best mode, and also to enable any person skilled in the art to make and use the invention. Certain terms have been used for brevity, clarity, and understanding. No unnecessary limitations are to be inferred therefrom beyond the requirement of the prior art because such terms are used for descriptive purposes only and are intended to be broadly construed. The patentable scope of the invention is defined by the claims and may include other examples that occur to those skilled in the art. Such other examples are intended to be within the scope of the claims if they have features or structural elements that do not differ from the literal language of the claims, or if they include equivalent features or structural elements with insubstantial differences from the literal languages of the claims.

What is claimed is:

1. A method for making a container for retaining anesthetic agent, the method comprising:
    creating two or more parts each having a mating surface, wherein the container is formed when the mating surfaces of the two or more parts are coupled together, and wherein a first part of the two or more parts is formed of a material having pores defined within the mating surface thereof;
    processing the mating surface of the first part by performing visco-plastic stirring with a friction stir welder to reduce the pores defined therein; and
    coupling the two or more parts together such that the mating surfaces contact to create the container configured to retain the anesthetic agent therein.

2. The method according to claim 1, wherein the two or more parts are coupled together via brazing.

3. The method according to claim 1, wherein the visco-plastic stirring creates a surface condition on the mating surface of the first part, further comprising processing the mating surface of the first part to remove the surface condition on the mating surface of the first part prior to coupling the two or more parts together.

4. The method according to claim 1, further comprising processing so as to flatten the mating surface of the first part prior to processing via the visco-plastic stirring.

5. The method according to claim 1, wherein the second part is also formed of a material having pores defined within the mating surface.

6. The method according to claim 1, wherein the material of the first part is a cast material.

7. The method according to claim 6, wherein the first part is sand casted.

8. The method according to claim 1, wherein the material of the first part is aluminum.

9. The method according to claim 1, wherein the container is a sump configured to retain a liquid as the anesthetic agent therein.

10. The method according to claim 1, wherein the two or more parts also have non-mating surfaces, further comprising applying a treatment to the non-mating surfaces prior to coupling the mating surfaces of the two or more parts together.

11. The method according to claim 1, wherein the treatment for the non-mating surfaces is nickel plating, and wherein the nickel plating of the non-mating surfaces is configured to be in contact with the anesthetic agent retained within the container.

12. The method according to claim 1, wherein a reservoir configured to retain the anesthetic agent is defined within the container when the two or more parts are coupled together, wherein a port is also defined within the container to communicate with the reservoir, and wherein the reservoir is air-tight other than via the port.

13. A method for making a container for retaining a gas or liquid, the method comprising:
    casting a first part of a metallic material, wherein the first part has a first mating surface and a non-mating surface, and wherein the metallic material has pores defined within the first mating surface;
    processing the first mating surface of the first part by performing visco-plastic stirring with a friction stir welder to reduce the pores defined therein;
    obtaining a second part made of a metallic material, the second part having a second mating surface and a second non-mating surface, wherein at least one of the first part and the second part defines a passageway; and
    brazing the first part and the second part together such that the first mating surface of the first part is in contact with the second mating surface of the second part;
    wherein a reservoir is formed between the first non-mating surface of the first part and the second non-mating surface of the second part when the first part and the second part are brazed together, wherein the reservoir is configured to retain the gas or liquid therein, and wherein the container is configured such that the gas or liquid exits the reservoir only via the passageway.

14. The method according to claim 13, wherein the step of brazing is oven brazing, wherein the reservoir is a sump, and wherein the metallic material of the first part is aluminum.

* * * * *